US011639037B2

(12) United States Patent
Klein

(10) Patent No.: US 11,639,037 B2
(45) Date of Patent: May 2, 2023

(54) PRODUCTION METHOD FOR A FIBER COMPOSITE COMPONENT

(71) Applicant: Robert Bosch GmbH, Stuttgart (DE)

(72) Inventor: Linda Klein, Esslingen (DE)

(73) Assignee: Robert Bosch GmbH, Stuttgart (DE)

( * ) Notice: Subject to any disclaimer, the term of this patent is extended or adjusted under 35 U.S.C. 154(b) by 364 days.

(21) Appl. No.: 16/924,491

(22) Filed: Jul. 9, 2020

(65) Prior Publication Data

US 2021/0010940 A1 Jan. 14, 2021

(30) Foreign Application Priority Data

Jul. 10, 2019 (DE) .................... 10 2019 210 171.2

(51) Int. Cl.
| | |
|---|---|
| *B29C 70/48* | (2006.01) |
| *G01N 21/75* | (2006.01) |
| *G16C 20/10* | (2019.01) |
| *B29C 70/68* | (2006.01) |
| *B29C 70/54* | (2006.01) |

(52) U.S. Cl.
CPC ............. *B29C 70/48* (2013.01); *B29C 70/54* (2013.01); *B29C 70/681* (2013.01); *G01N 21/75* (2013.01); *G16C 20/10* (2019.02)

(58) Field of Classification Search
None
See application file for complete search history.

(56) References Cited

FOREIGN PATENT DOCUMENTS

| DE | 10 2006 035 274 A1 | 2/2008 | |
|---|---|---|---|
| DE | 102009056895 A1 * | 6/2011 | ........... B29C 70/865 |
| DE | 10 2016 220 032 A1 | 4/2018 | |
| WO | 2018/069066 A1 | 4/2018 | |

OTHER PUBLICATIONS

Machine English translation of DE102009056895 Spec, Accessed Dec. 6, 2022 (Year: 2011).*
Machine English translation of DE102009056895 Claims, Accessed Dec. 6, 2022 (Year: 2011).*
Machine English translation of DE102006035274, Accessed Dec. 6, 2022 (Year: 2008).*

* cited by examiner

*Primary Examiner* — Jacob T Minskey
*Assistant Examiner* — Adrianna N Konves
(74) *Attorney, Agent, or Firm* — Maginot, Moore & Beck LLP

(57) ABSTRACT

A method for producing a fiber composite component is disclosed. A sensor device having a flexible circuit carrier and/or a sensor module is integrated in the fiber composite component. The method comprises: loading a tool configured to produce the fiber composite component with textile layers and the sensor device; closing the loaded tool and compressing the textile layers and the sensor device; introducing a liquid matrix into the closed tool and impregnating the textile layers to produce the fiber composite component; detecting an acceleration in relation to the closing of the tool and/or the introducing of the liquid matrix, using at least one of the sensor device and the sensor module of the sensor device; and determining a process state and/or a process parameter based on a spectral analysis of the detected acceleration in a frequency domain.

9 Claims, 4 Drawing Sheets

PRODUCTION METHOD FOR A FIBER COMPOSITE COMPONENT

This application claims priority under 35 U.S.C. § 119 to application no. DE 10 2019 210 171.2, filed on Jul. 10, 2019 in Germany, the disclosure of which is incorporated herein by reference in its entirety.

TECHNICAL FIELD

The present disclosure relates to a production method for a fiber composite component, a correspondingly produced fiber composite component, a test method for a correspondingly produced fiber composite component, a computer program and machine-readable storage medium corresponding thereto, and also a device corresponding thereto.

BACKGROUND

WO 2018/069066 A1 discloses a method for arranging a number of micromechanical acceleration sensors on or in a plastics component, in particular a fender, and a corresponding plastics component, in particular fender.

In step A of the method, the micromechanical acceleration sensor is fixedly positioned into or onto a flexible circuit carrier, wherein the micromechanical acceleration sensor is contacted with an integrated conductor track structure of the flexible circuit carrier.

In step B of the method, at least regionally the micromechanical acceleration sensor and the flexible circuit carrier are arranged onto or into the plastics component in such a way that the integrated conductor track structure of the flexible circuit carrier is at least partly exposed.

DE 10 2016 220 032 A1 discloses a sensor device for a vehicle, in particular a motor vehicle, comprising at least one sensor module and comprising at least one connecting line connected to the sensor module, for electrically contacting the sensor module.

Provision is made for the connecting line to be embodied as a conductor film on which a plurality of different sensor modules are arranged and contacted by a respective conductor film or a common conductor film.

In the course of producing fiber composite structures, such as fiber composite components, by methods such as Liquid Composite Molding (LCM) or Liquid Resin Injection (LRI), by way of various approaches sensor technologies are used to detect the states during the production process steps. For this process monitoring, in one instance, sensors, so-called Tool Mounted Sensors (TMS), are introduced into the production tool.

However, said sensors leave behind traces on the end product; moreover, they may lose contact with the component, said contact being required for the sensing, owing to the shrinkage of the resin introduced into the tool.

In another instance, non-contact measurement methods are a solution to this problem. However, these methods cannot always be realized.

As an alternative thereto, sensors are integrated directly into the structural construction in the tool. Variables that are monitored during the process monitoring are usually the flow front (for checking complete matrix infusion), impregnation throughout the inserted textile fibers or the textile semifinished product (textile layers) and the degree of curing of the structural component composed of matrix and fibers or textile semifinished product.

Dielectric and optical or thermal measurement methods can be used for this purpose.

Typical measurement methods are direct voltage analysis (DC analysis), dielectric analysis (DEA) or electrical time domain reflectometry (ETDR).

To that end, use is made of DC point sensors or electrodes introduced in the tool or structural component, for example. It is also known to use the SMARTweave method on the basis of fiber-based planar electrodes of grids of a plurality of dielectric sensors, of carbon fibers or of specially developed buckypapers composed of entangled Carbon Nano Tube (CNT) strands, of specially developed two-conductor sensors or of Fringing Electric Field Sensors (FEF sensors), which measure material properties as a function of location and time.

In order to detect the propagation of the flow front or the mold filling or the degree of curing of the fiber composite component, the thermodynamic and/or mechanical properties of the matrix are also used. This is done using pressure pickups or (micro-) thermoelements. Optical detection of the flow front is possible using Fiber Optical Sensors (FOS), Optical Fiber Refractometers (OFR), optical fiber interferometers (OFI) or (fiber optical) spectrometers that are integrated in the structural construction.

For a non-contact measurement method in the tool mold, use is made of ultrasound, e.g. by way of ultrasonic transducers or an introduced copper wire.

Further possible sensor technologies based on electrical measurement principles are direct current resistance (DCR) sensors, conductive filaments, microbraidings or Fiber Bragg Grating (FBG) sensors.

Furthermore, thermography is suitable for determining the degree of curing.

SUMMARY

Against this background, the present disclosure provides a method for producing a fiber composite component. A sensor device is integrated in the fiber composite component, i.e. arranged within the fiber composite component. The sensor device has a flexible circuit carrier and/or a sensor module. The method comprises the following steps:

The flexible circuit carrier can have one or a plurality of sensor modules.

Loading a tool for producing the fiber composite component with textile layers, i.e. with textile fibers or a textile semifinished product, and the sensor device.

Closing the loaded tool and compressing the textile layers and the sensor device.

Introducing a liquid matrix (matrix infusion) for producing the fiber composite component.

Detecting an acceleration in relation to a production step, in particular to closing the tool and/or introducing the matrix into the tool cavity and/or impregnating the textile layers in the tool, and/or opening the tool, by means of the sensor device or the sensor module of the sensor device.

In this case, the detection of the acceleration can be effected by way of an event during the production of the fiber composite component.

Deriving and/or evaluating a process state and/or a process parameter of the production method depending on the detected acceleration.

With a process state typically being controlled or set by way of one or a plurality of process parameters.

The method is distinguished by the fact that the deriving and/or the evaluating are/is carried out on the basis of a spectral analysis of the detected acceleration in the frequency domain.

In this case, it is conceivable to carry out the spectral analysis in the discrete frequency domain.

The detected acceleration in the frequency domain, that is to say the frequency spectra of the acceleration or the acceleration signal thereof, can be analyzed with respect to characteristic variables, both qualitatively and quantitatively. Significant changes in the characteristic are sought in this case:

For example the location or the frequency at which maximum spectral components occur can be considered.

For example the size, that is to say the magnitudes, of the maximum spectral components can be considered.

For example the appearance of the envelopes of the spectral components over the frequency response can be considered.

For example the areas beneath the envelopes over the frequency response in the vicinity of the maximum spectral components can be considered.

For example the gradient of the envelopes over the frequency response in the vicinity of the maximum spectral components can be considered.

For example the area sum over all the spectral components beneath the envelopes of the spectral components over the frequency response can be considered.

The method has the advantage that as a result of the analysis of the test signal in the frequency domain, i.e. following the spectral analysis, features of the signal become better visible, or actually visible in the first place, in comparison with the signal in the time domain.

The evaluation of the derived process states and/or of the process parameters can be used for the optimization thereof (process optimization). This concerns, in particular, avoiding an inadequate component quality during production. An inadequate quality during the production of fiber composite components can lead to internal inhomogeneity and damage in the component. This can influence the mechanical performance of the component and the component reliability. In the present case, a fiber composite component can be understood to mean a component that consists of a fiber composite material. A fiber composite material generally arises as a result of an interacting composite composed of textile fibers or a textile semifinished product and a matrix between the fibers or the textile semifinished product. The matrix is filler and adhesive. What is typical of fiber composite materials is that the interaction of the composite gives rise to a material having properties of higher quality in comparison with the properties of the fibers and the matrix.

The fiber composite component can be a body part for a vehicle; e.g. a fender component or a component of the longitudinal side of the vehicle.

The fiber composite component can be a component from, inter alia, the field of mechanical and plant engineering, medical technology, the fields of aviation and space engineering, energy, offshore, robotic, sports equipment and consumer products.

Furthermore, the fiber composite component can be a piece of sports equipment.

A flexible circuit carrier can comprise, inter alia, silicones, polyurethanes, polyamides, or thermoplastics. In this regard, the flexible circuit carrier can be deformed flexibly; in particular, the integrated conductor track structure can be correspondingly deformed plastically, as a result of which substantially the flexible circuit carrier can be adapted to a geometry or shape of the fiber composite component. The flexible circuit carrier can be a conductor film.

The sensor module can be an electronic and/or electrical component for detecting an acceleration, i.e. an acceleration sensor module. The sensor module can be a micromechanical sensor module. The sensor module can be a micromechanical sensor module in the manner of microelectromechanical systems (MEMS).

A sensor module for detecting an acceleration, e.g. a micromechanical acceleration sensor in the manner of microelectromechanical systems (MEMS), generally outputs a signal in the form of an acceleration over time, that is to say a signal in the time domain.

On account of the measurement characteristic of the micromechanical acceleration sensor, an event in the course of the production of the component into which the acceleration sensor is integrated in the form of a sensor device may not be able to be identified sufficiently accurately on the basis of a variation in the profile of the time signal (acceleration over time). This is dependent on the intensity of the event.

The production steps of, inter alia, loading, closing, introducing, impregnating and opening have a mandatory order corresponding to the order presented.

The steps of detecting and deriving can be effected in parallel with the production steps. These steps can be effected multiply or regularly or permanently or continuously during the production method.

The disclosure is based on the insight that a sensor device that is arranged in a fiber composite component and detects an acceleration, during the process of introducing a liquid matrix for producing the fiber composite component, is momentarily deflected or accelerated or excited, in particular by the incoming flow front. In the event of detection of the acceleration in real time and assessment or analysis of the signal, this cannot be identified in a simple manner, or cannot be identified at all, in the sensor signal in the time domain. Therefore, the present disclosure is distinguished by carrying out the derivation and evaluation of the detected signal on the basis of a spectral analysis in the frequency domain. The deflection or acceleration thus detected allows a conclusion to be drawn about the incoming melt (the liquid matrix). As a result, by way of the detected acceleration signal, the process parameters of resin injection (such as injection pressure, rate or temperature) or the point in time of resin injection in the overall process of the production method can be derived, evaluated and optimized by means of the sensor device that is arranged or integrated into the fiber composite component produced in this case. The detected acceleration signal can furthermore be used for checking or evaluating the process parameters used in the production process and thus also for checking and evaluating the product produced.

The steps of detecting and deriving and/or evaluating can also be effected in relation to impregnating the textile layers.

Furthermore, as early as upon closing the tool, effects can be detected in the sensor signal and the process parameters for closing the tool (closing speed or force, inter alia) in the production method or the point in time of closing in the overall process can likewise be derived and/or evaluated therefrom. By way of example, the point in time of closing the tool can be identified in the detected acceleration signal.

The evaluation of the derived process parameters can be used for the optimization thereof.

The closing can be effected in such a way that the tool with the received textile fibers or the textile semifinished product (textile layers) and the received sensor device is effected in an airtight manner, e.g. by means of screw or compressive/pressure force.

The liquid matrix can be a resin. The resin can be a pure resin.

The detection of the acceleration can be effected in real time.

By means of the method according to the present disclosure, in the course of producing a fiber composite component sensor device that is arranged in a fiber composite component and detects an acceleration, a secondary additional function of monitoring the production process is already realized during the production of the component.

According to one embodiment of the production method according to the present disclosure, the method comprises the additional step of opening the tool after the step of introducing the matrix and subsequently curing the fiber composite component in the tool, wherein the steps of detecting and deriving and/or evaluating are also effected in relation to opening.

The evaluation of the derived process parameters can be used for the optimization thereof.

Furthermore, it is advantageous if zero padding of the detected acceleration in the time domain is effected in the context of the spectral analysis.

In the present case, zero padding is understood to mean that the detected acceleration in the time domain is filled with zeros. The observation interval can be enlarged as a result, whereby narrower sampling can be achieved e.g. following the application of fast Fourier transformation for the spectral analysis. Although an increase in the quality of the detected acceleration cannot be achieved as a result of this, a better representation of the signal in the frequency domain is possible as a result of the narrower sampling.

A further aspect of the present disclosure is a fiber composite component. The fiber composite component comprises a sensor device with a flexible circuit carrier and/or a sensor module and is produced by means of a production method according to the present disclosure.

The sensor module can be an electronic and/or electrical component for detecting an acceleration, i.e. an acceleration sensor module. The sensor module can be a micromechanical sensor module. The sensor module can be a micromechanical sensor module in the manner of microelectromechanical systems (MEMS).

A further aspect of the present disclosure is a method for testing a fiber composite component. A sensor device with a flexible circuit carrier and/or a sensor module is integrated in the fiber composite component. The method comprises the following steps:

Detecting an acceleration by means of the sensor device or the sensor module of the sensor device.

Determining the degree of curing of the fiber composite component depending on the detected acceleration.

The method is distinguished by the fact that in the step of determining, the determination of the degree of curing is carried out on the basis of a spectral analysis in the frequency domain.

In this case, it is conceivable to carry out the spectral analysis in the discrete frequency domain.

The test method can be carried out during the curing of a fiber composite component in the context of the production thereof. This can involve the curing during the production of a fiber composite component according to the production method according to the present disclosure.

The method has the advantage that as a result of the analysis of the detected acceleration in the frequency domain, i.e. following the spectral analysis, features of the detected acceleration in the frequency domain become better visible, or actually visible in the first place, in comparison with the signal in the time domain.

A more accurate test of the fiber composite component can be performed as a result. In this regard, disadvantageous inserts into the fiber composite component or disadvantageous states of the fiber composite component can be better identified. One disadvantageous state not caused by a disadvantageous insert, for example, is an insufficient degree of curing. Such inserts or states may have occurred as early as in the method for production of the fiber composite component or in the later course of the life of the fiber composite component, e.g. during use on a vehicle if the fiber composite component is a body component of the vehicle.

The fiber composite component to be tested can be a fiber composite component according to the present disclosure.

The sensor module can be an electronic and/or electrical component for detecting an acceleration, i.e. an acceleration sensor module. The sensor module can be a micromechanical sensor module. The sensor module can be a micromechanical sensor module in the manner of microelectromechanical systems (MEMS).

The detecting can be effected in reaction to a predetermined impulse being applied to the fiber composite component and/or the tool for producing a fiber composite component having the fiber composite component to be tested.

According to one embodiment of the test method according to the present disclosure, the method comprises the step of comparing the detected acceleration with a reference acceleration. In the step of determining, the degree of curing is then determined depending on the comparison or the comparison result.

The reference signal can be generated by a procedure in which the fiber composite component is caused to effect a reference oscillation and the reference oscillation is detected by means of the sensor device and the detected signal or a signal derived therefrom is the reference signal.

The reference signal is used for follow-up examinations or tests of the fiber composite component.

It is advantageous if the reference signal is generated in a new state, in particular in a fully cured state, of the fiber composite component. As a result, a deviating from the fully cured state or a variation of the component characteristics can be ascertained during a later effected test of the fiber composite component in accordance with the method of the present disclosure by means of the comparison of the test signal with the reference signal. On the basis of the component characteristics ascertained, it is possible to deduce the state and/or a change in state of the component at the point in time of carrying out the method for testing the fiber composite component in comparison with the new state thereof or the fully cured state thereof. A suitable measure can be implemented with this information.

The state thus determined and/or said change in state thus determined for the fiber composite component can be output by means of a state signal that suitably represents the state and/or the change in state.

According to one embodiment of the method of the present disclosure, in the step of comparing in the course of the spectral analysis, the detected acceleration and the reference signal are considered only one-sidedly.

This is appropriate since the periodicity of the signal is utilized, such that in the course of the (discrete) Fourier transformation the spectrum of the signal is considered over only one period. One period extends over the frequency range from 0 to the sample rate of the signal. Since the spectrum of the signal is present symmetrically around the center point after the (discrete) Fourier transformation, the information obtained is also present in a redundant fashion, as a result of which a one-sided consideration is sufficient.

According to one embodiment of the method of the present disclosure, in the step of determining, the determination is effected depending on significant changes in the characteristic of the frequency spectrum.

According to the present disclosure, significant is understood to mean all changes that go beyond the scope of the measurement accuracy of the integrated sensor module or of the sensor device—known per se—and are thus not attributable to the measurement uncertainty.

According to one embodiment of the method of the present disclosure, the detected acceleration lies within a considered measurement range of the sensor device and is dependent on a natural frequency of the surroundings of the fiber composite component.

In the present case, surroundings can be understood to mean, for example, the tool or the peripheral connections during the production of the fiber composite component, a device for clamping the fiber composite component, the device for suspending the fiber composite component on a vehicle, but also other frequency transmissions which influence the detection of the test signal.

For an accurate signal analysis, when the component is caused to effect a test oscillation, the natural frequencies of the surroundings should be outside the measurement range (frequency domain) of the sensor module. Particularly if the acceleration sensor has a high- or low-pass filter. This can be effected by means of an oscillation isolation, for example.

This ensures that during the analysis of the frequency response of the acceleration sensor signal, no frequency components are superimposed by natural oscillation of the surroundings.

A further aspect of the present disclosure is a computer program configured to carry out the steps of the test method according to the present disclosure.

A further aspect of the present disclosure is a machine-readable storage medium on which a computer program according to the present disclosure is stored.

A further aspect of the present disclosure is a device configured to carry out the steps of the test method according to the present disclosure.

BRIEF DESCRIPTION OF THE DRAWINGS

Further features and advantages of the aspects of the present disclosure are explained below on the basis of embodiments with reference to the figures.

In the figures.

DETAILED DESCRIPTION

Figure 1A:
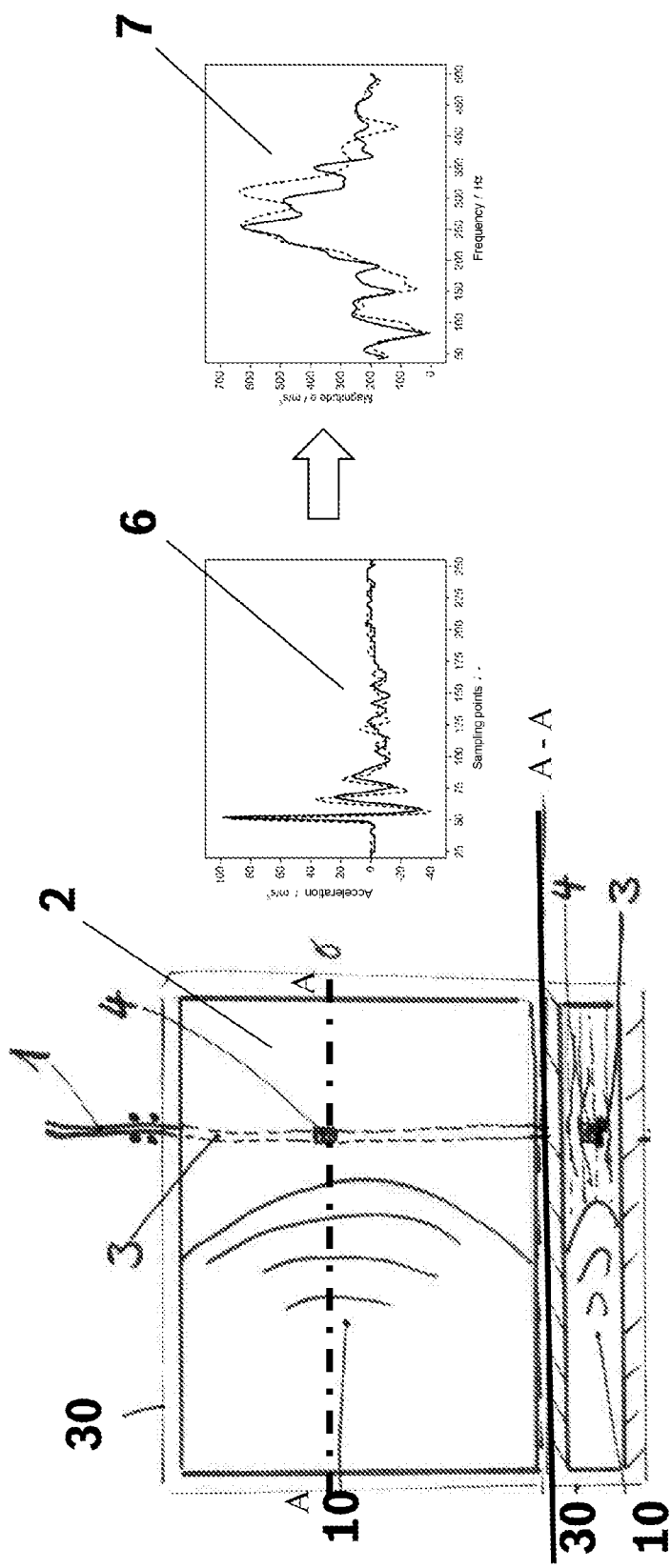
FIGS. 1a, 1b show schematic illustrations of a process step during the production of a fiber composite component according to the present disclosure (view into the interior of the tool/section through the tool)

FIG. 1a shows a schematic illustration of a process step during the production of a fiber composite component 2 according to the present disclosure. The illustration shows a process step during production in a Liquid Composite Molding (LCM) method of a fiber composite component 2 comprising a sensor device 1 with a flexible circuit carrier 3 and/or a sensor module 4, said sensor device being arranged in the fiber composite component 2. The process step illustrates the melt flow (matrix flow or resin flow) at an early point in time after resin injection 10.

The upper part of the illustrated view is a plan view of the tool 30 (view into the interior of the tool/section through the tool). The lower part is a side view of the tool 30 on the sectional axis A-A.

A signal profile 6 of the sensor device 1 or of the acceleration detected by the sensor module 4 in the time domain is plotted schematically alongside the views of the tool 30.

The acceleration 6 detected in the time domain is converted into the frequency domain 7 in the context of process monitoring or process optimization for spectral analysis. This is illustrated in FIG. 1a on the basis of the illustration of the envelopes 7 of the frequency components of the detected signal profile 6.

The signal profiles in the time domain 6 and in the frequency domain 7 illustrated by means of the solid line represent the signal profile that was detected shortly before the arrival of the melt 10 at the sensor device 1 or the sensor module 4.

Figure 1B:
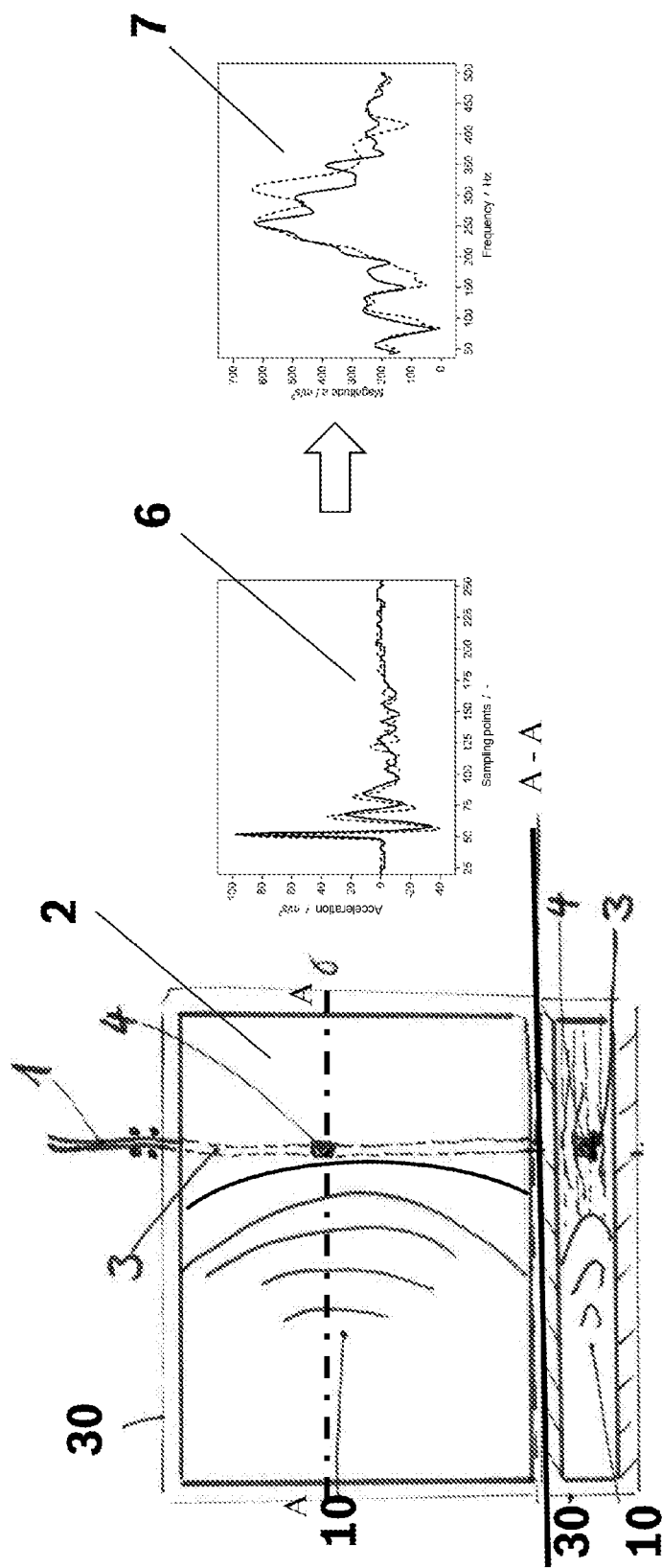

FIG. 1b shows a schematic illustration of a process step during the production of a fiber composite component 2 according to the present disclosure. The process step illustrates the point in time directly upon the arrival of the melt flow (matrix flow or resin flow) 10 at the sensor module 4.

The upper part of the illustrated view is a plan view of the tool 30. The lower part is a side view of the tool 30 on the sectional axis A-A.

A signal profile 6 of the sensor device 1 or of the acceleration detected by the sensor module 4 in the time domain is plotted schematically alongside the views of the tool 30. The acceleration detected in the time domain is converted into the frequency domain in the context of process monitoring or process optimization for spectral analysis. This is illustrated in FIG. 1b on the basis of the illustration of the envelopes 7 of the frequency components of the detected signal profile 6.

The signal profiles in the time domain 6 and in the frequency domain 7 illustrated by means of the dashed line represent the signal profile that was detected directly upon the arrival of the melt 10 at the sensor device 1 or the sensor module 4.

It is readily evident from the illustrations that the representation in the frequency domain permits significantly more and significantly clearer evaluations of the sensor signal profile by comparison with the signal profile in the time domain.

The method has the advantage that as a result of the analysis of the detected acceleration or of the sensor signal 7 in the frequency domain, i.e. following the spectral analysis, features of the sensor signal become better visible, or actually visible in the first place, in comparison with the signal in the time domain 6.

In this regard, process states and/or process parameters can be derived more easily. The evaluation of the derived process parameters can be used for the optimization thereof (process optimization).

Figure 2:
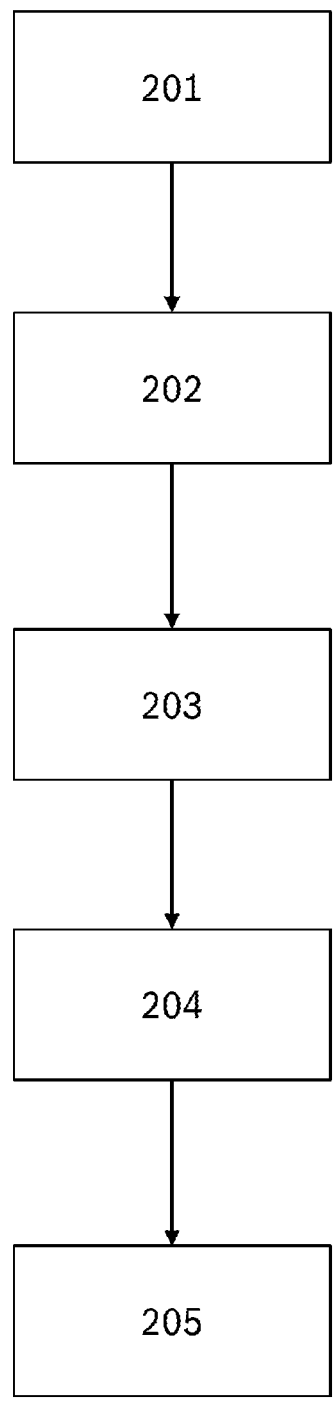
FIG. 2 shows a flow diagram of a production method according to the present disclosure.

FIG. 2 shows a flow diagram of a production method 200 according to the present disclosure.

The production method 200 is suitable for producing a fiber composite component 2 in which a sensor device 1 with a flexible circuit carrier 3 and/or a sensor module 4 is arranged or integrated.

The method 200 comprises the following steps 201 to 205 illustrated in FIG. 2.

In step 201, a tool 30 for producing the fiber composite component 2 is loaded with textile fibers or a textile semi-finished product (textile layers) and the sensor device 1.

In step 202, the loaded tool 30 is closed and the textile layers and the sensor device 1 are compressed.

The tool 30 can be closed in an airtight manner.

In step 203, a liquid matrix 10 is introduced into the closed tool 30 for producing the fiber composite component 2.

The matrix 10 can be a resin. The resin can be a pure resin.

Step 204 involves detecting an acceleration 6 in relation to introducing in 203 and/or closing the tool 302 by means of the sensor device 1 or the sensor module 4 of the sensor device 1.

The detecting 204 can be effected in real time.

In step 205, the process parameters of the production method 300 are derived, evaluated depending on the detected acceleration 6. In this case, the deriving and evaluating are effected on the basis of a spectral analysis of the detected acceleration 6 in the frequency domain 7.

The steps of loading 201, closing 202 and introducing 203 have a mandatory order corresponding to the order presented. The steps of detecting 204 and deriving, evaluating and optimizing 205 can be effected in parallel with the other steps 201 to 203 of the method 200. These steps 204, 205 can be effected multiply or regularly or permanently or continuously during the production method 200.

Figure 3:
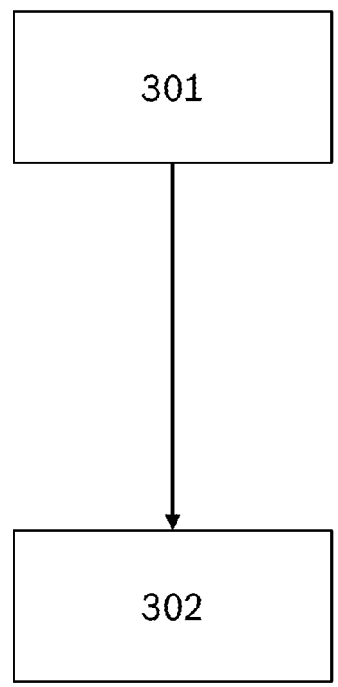
FIG. 3 shows a flow diagram of a test method according to the present disclosure.

FIG. 3 shows a flow diagram of a test method according to the present disclosure.

The test method 300 can be effected during the curing in the tool 30 in the context of the production of a fiber composite component 2 according to the present disclosure. The fiber composite component 2 has a sensor device 1 with one or a plurality of flexible circuit carriers 3 and/or one or a plurality of sensor modules 4. The fiber composite component 2 may have been produced or be produced according to the production method 200 according to the present disclosure.

In step 301, an acceleration 6 is detected by means of the sensor device 1 or the sensor module 4 of the sensor device 1.

The step of detecting 301 can be effected in reaction to a predetermined impulse being applied to the fiber composite component 2 to be tested and/or to a tool 30 for producing a fiber composite component 2 having the fiber composite component 2 to be tested.

In step 302, a degree of curing of the fiber composite component 2 to be tested is determined depending on the detected acceleration 6. In this case, the determination of the degree of curing is effected on the basis of a spectral analysis of the detected acceleration 6 in the frequency domain 7.

What is claimed is:

1. A method for producing a fiber composite component, a sensor device having at least one of a flexible circuit carrier and a sensor module being integrated in the fiber composite component, the method comprising:

loading a tool configured to produce the fiber composite component with textile layers and the sensor device;

closing the loaded tool and compressing the textile layers and the sensor device;

introducing a liquid matrix into the closed tool and impregnating the textile layers to produce the fiber composite component;

detecting an acceleration in relation to at least one of the closing of the tool and the introducing of the liquid matrix, using at least one of the sensor device and the sensor module of the sensor device; and determining at least one of a process state and a process parameter based on a spectral analysis of the detected acceleration in a frequency domain.

2. The method according to claim 1 further comprising:
opening the tool after introducing the liquid matrix,
wherein detecting the acceleration and determining the at least one of the process state and the process parameter is also effected in relation to at least one of the impregnating of the textile layers and the opening of the tool.

3. The method according to claim 1, the determining of the at least one of the process state and the process parameter further comprising:
zero padding in a time domain.

4. The method according to claim 1, where the sensor module is a micromechanical acceleration sensor module.

5. The method according to claim 1, the closing the loaded tool further comprising:
closing the loaded tool in an airtight manner.

6. The method according to claim 1, where the liquid matrix is a resin.

7. The method according to claim 6, where the resin is a pure resin.

8. The method according to claim 1, the detecting the acceleration further comprising:
detecting the acceleration in real time.

9. The method according to claim 1, the determining the at least one of the process state and the process parameter further comprising:
determining the at least one of the process state and the process parameter based on a spectral analysis of the detected acceleration in a discrete frequency domain.

* * * * *